(12) United States Patent
Hwang et al.

(10) Patent No.: US 8,415,499 B2
(45) Date of Patent: Apr. 9, 2013

(54) DYES FOR DYE-SENSITIZED SOLAR CELL AND DYE-SENSITIZED SOLAR CELL USING THE SAME

(75) Inventors: Jinok Hwang, Seoul (KR); Seongkee Park, Goyang-si (KR); Sunghoon Joo, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 633 days.

(21) Appl. No.: 12/654,042

(22) Filed: Dec. 8, 2009

(65) Prior Publication Data

US 2010/0210863 A1    Aug. 19, 2010

(30) Foreign Application Priority Data

Feb. 16, 2009  (KR) .......................... 10-2009-0012392

(51) Int. Cl.
*C07C 211/57*    (2006.01)
(52) U.S. Cl.
USPC ............................ 564/305; 548/400; 368/205
(58) Field of Classification Search ................... 548/400, 548/439; 549/29, 356; 514/408, 411, 438, 514/451; 368/205; 564/305
See application file for complete search history.

(56) References Cited

PUBLICATIONS

Thomas, et al "Organic dyes containing theinylfluorene conjugation for solar cells," Chem. Commun. (2005), pp. 4098-4100.*

* cited by examiner

*Primary Examiner* — Kamal Saeed
*Assistant Examiner* — Janet L Coppins
(74) *Attorney, Agent, or Firm* — McKenna Long & Aldridge LLP

(57) ABSTRACT

Dyes for a dye-sensitized solar cell are provided. The dyes for a dye-sensitized solar cell have a structure of

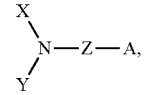

wherein each of X and Y independently comprises a substituent, comprising a substituted or unsubstituted aromatic hydrocarbon group, a substituted or unsubstituted aromatic heterocyclic group, and combinations thereof, and at least one of the X and Y comprises an aromatic group which are substituted a pyrene derivative substituted with an alkyl group or an aryl group, and Z comprises a substituted or unsubstituted aromatic hydrocarbon group, a substituted or unsubstituted heterocyclic group, a vinyl group, and a substituted or unsubstituted polyvinyl group, and A comprises an acid functional group.

5 Claims, 1 Drawing Sheet

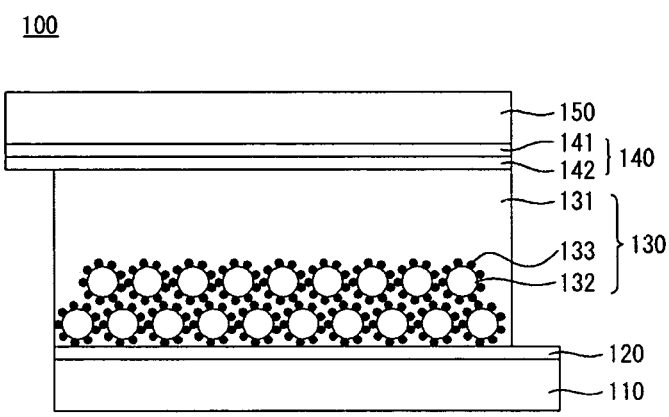

DYES FOR DYE-SENSITIZED SOLAR CELL AND DYE-SENSITIZED SOLAR CELL USING THE SAME

This application claims the benefit of Korean Patent Application No. 10-2009-0012392 filed on Feb. 16, 2009, which is hereby incorporated by reference for all purposes as if fully set forth herein.

BACKGROUND OF THE INVENTION

1. Field of the Invention

This document relates to a solar cell, and more particularly, to dyes for a dye-sensitized solar cell.

2. Discussion of the Related Art

Nowadays, in order to solve a facing energy problem, various researches for energy that can replace existing fossil fuels have been advanced. Particularly, various researches for using nature energy such as a wind force, atomic energy, and solar energy for replacing petroleum resources to be exhausted within several decades have been advanced.

Because a solar cell uses solar energy, which is an infinite and environmental-friendly energy source, unlike other energy sources, the solar cell has been in the spotlight due to an energy shortage problem since a Si solar cell was developed in 1983.

However, due to a supply and demand problem of a Si raw material, such a silicon solar cell causes a keen competition between countries and has a high production cost. Many foreign and domestic research institutions suggest solving means for solving the problems, but it is still difficult to solve the problems. An alternative for solving such a serious energy problem is a dye-sensitized type solar cell, and the dye-sensitized type solar cell was developed by Dr. Micheal Graetzel's research team of Switzerland National 'Ecole Polytechnique Federale de Lausanne' (EPFL) in 1991 and has been in the spotlight in the academic world and has been researched by many research institutions.

Unlike a silicon solar cell, the dye-sensitized solar cell is a photoelectric chemical solar cell using photosensitive dye molecules for generating electron-hole pairs by absorbing visible rays and using a transition metal oxide for transferring generated electrons as a main constituent material. A typical dye-sensitized solar cell among conventional dye-sensitized solar cells is a dye-sensitized solar cell using a nano particle titanium oxide.

The dye-sensitized solar cell can be applied to an outer wall glass window of a building or a glass green house due to a cheap production cost and a transparent electrode, compared with an existing silicon solar cell, but due to low photoelectric conversion efficiency, a more research is necessary.

Because photoelectric conversion efficiency of a solar cell is proportional to the quantity of electrons generated due to absorption of sun light, in order to increase photoelectric conversion efficiency, by increasing a dye amount to be adsorbed to nano particles of a titanium oxide, a generation amount of electrons is increased, absorption of sun light is increased, and the generated excited electron should be prevented from being disappeared by an electron-hole recombination.

In order to increase a dye adsorption amount per unit area, an oxide semiconductor particle should be produced to a size of a nanometer level, and in order to increase absorption of sun light, a method of increasing a reflectivity of a platinum electrode or of mixing semiconductor oxide light scattering particles having a size of several micrometers to the dyes was developed.

However, because a conventional method has a limitation in improving photoelectric conversion efficiency of a solar cell, new technical development for improving photoelectric conversion efficiency is urgently requested.

SUMMARY OF THE INVENTION

An aspect of this document is to provide dyes for a dye-sensitized solar cell having excellent photoelectric conversion efficiency and lifetime characteristics and a solar cell comprising the same.

Dyes for a dye-sensitized solar cell in an implementation of this document have a structure of chemical formula 1.

Dyes for a dye-sensitized solar cell having a structure of chemical formula 1.

[Chemical formula 1]

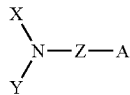

wherein each of X and Y independently comprises a substituent, comprising a substituted or unsubstituted aromatic hydrocarbon group, a substituted or unsubstituted aromatic heterocyclic group, and combinations thereof, and at least one of the X and Y comprises an aromatic group which are substituted pyrene derivative substituted with an alkyl group or an aryl group, and Z comprises a substituted or unsubstituted aromatic hydrocarbon group, a substituted or unsubstituted heterocyclic group, a vinyl group, and a substituted or unsubstituted polyvinyl group, and A comprises an acid functional group.

BRIEF DESCRIPTION OF THE DRAWINGS

The accompany drawings, which are comprised to provide a further understanding of the invention and are incorporated on and constitute a part of this specification illustrate embodiments of the invention and together with the description serve to explain the principles of the invention.

FIG. 1 is a cross-sectional view illustrating a dye-sensitized solar cell in an implementation of this document.

DETAILED DESCRIPTION OF THE ILLUSTRATED EMBODIMENTS

Reference will now be made in detail embodiments of the invention examples of which are illustrated in the accompanying drawings.

Dyes for a dye-sensitized solar cell in an implementation of this document have a structure of chemical formula 1.

[Chemical formula 1]

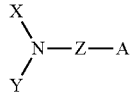

wherein each of X and Y independently comprises a substituent, comprising a substituted or unsubstituted aromatic hydrocarbon group, a substituted or unsubstituted aromatic heterocyclic group, and combinations thereof, and at least one of the X and Y comprises an aromatic group which are substituted pyrene derivative substituted with an alkyl group or an aryl group, and Z comprises a substituted or unsubstituted aromatic hydrocarbon group, a substituted or unsubstituted heterocyclic group, a vinyl group, and a substituted or unsubstituted polyvinyl group, and A comprises an acid functional group.

Each of the X and Y independently comprises a substituent, comprising a substituted or unsubstituted aromatic hydrocarbon group having a carbon number of 5 to 20, a substituted or unsubstituted aromatic heterocyclic group, and combinations thereof, and at least one of the X and Y comprises a pyrene derivative substituted with one selected from a group consisting of an alkoxy group, an alkenyl group, an arylene group, and an alkylene group.

The X and Y may comprise a substituent selected from a group consisting of alkyl, alkoxy, an aryl group, an arylene group, an alkylene group, and combinations thereof.

The Z may comprise a substituent selected from a group consisting of thiophene, a vinyl group, a polyvinyl group, benzene, naphthalene, anthracene, fluorene, biphenyl, pyran, pyrrole, carbazole, and combinations thereof.

The Z may be a substituent selected from a group consisting of alkyl, alkoxy, an aryl group, an alkenyl group, an arylene group, an alkylene group, and combinations thereof.

The A may comprise a substituent selected from a group consisting of a carboxylic acid group, a phosphorous acid group, a sulfonic acid group, a phosphinic acid group, a hydroxy acid group, an oxycarboxylic acid group, and combinations thereof.

The X—N—Y may be one of the following compounds.

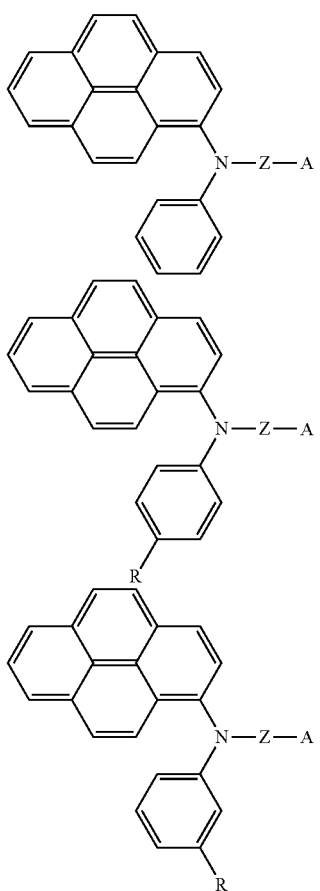

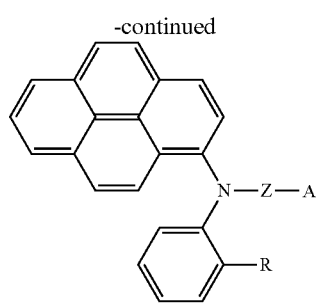

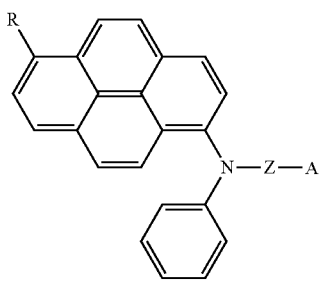

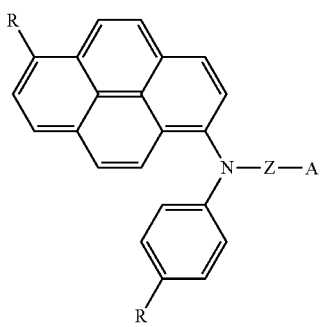

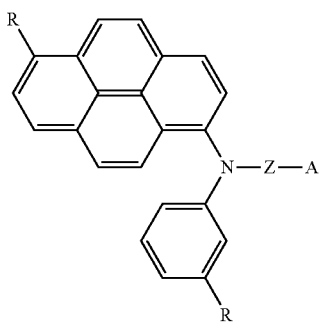

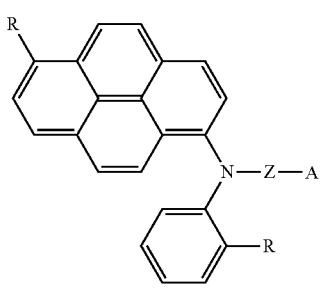

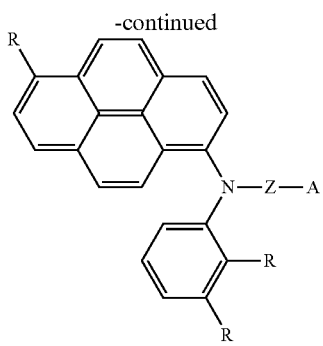
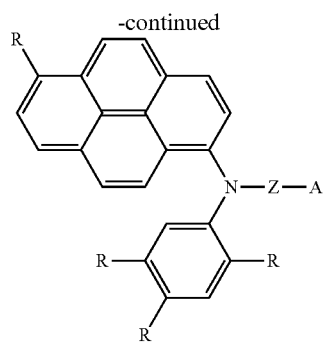
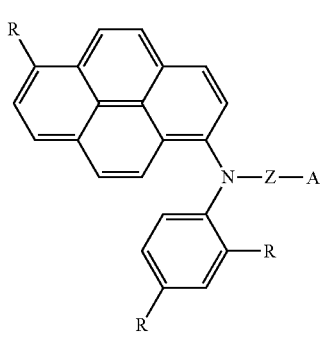
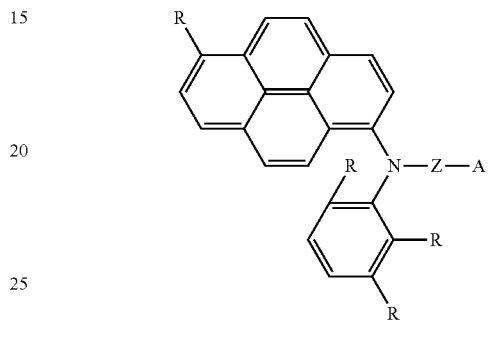
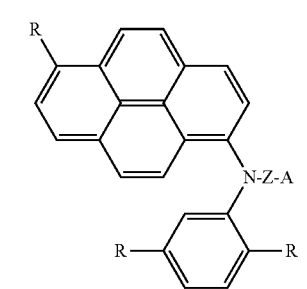
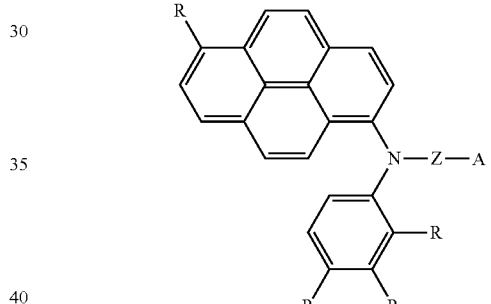
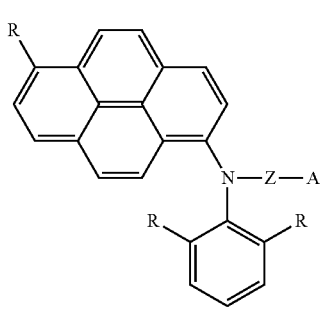
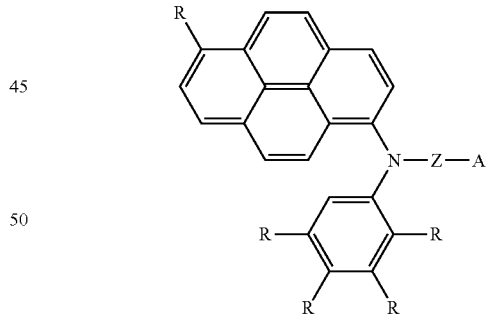
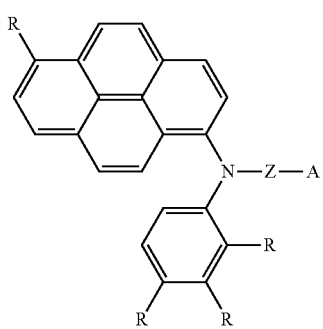
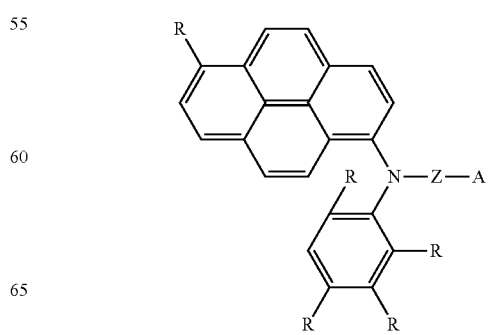

-continued

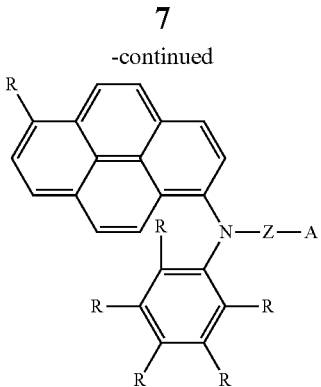

where R may be formed with one selected from a group consisting of H, an alkyl group of C1 to C8, an alkoxy group, an aryl group, an alkenyl group, an arylene group, an alkylene group, and $SiR_13$ ($R_1$ is an alkyl group of C1 to C8), or combinations thereof, and the R may be different from each other,

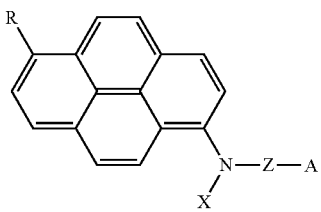

where N—X may be one of the following compounds,

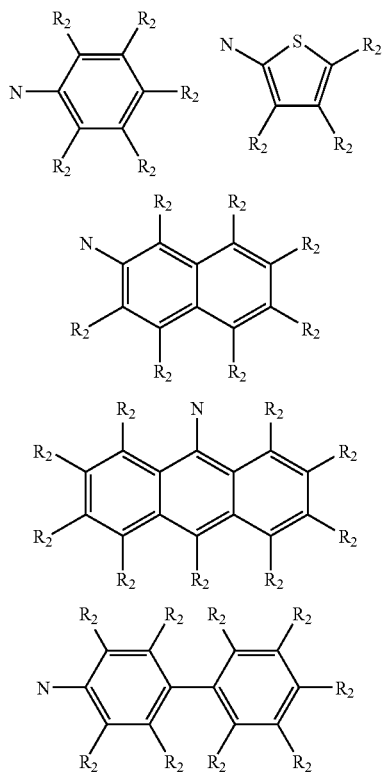

-continued

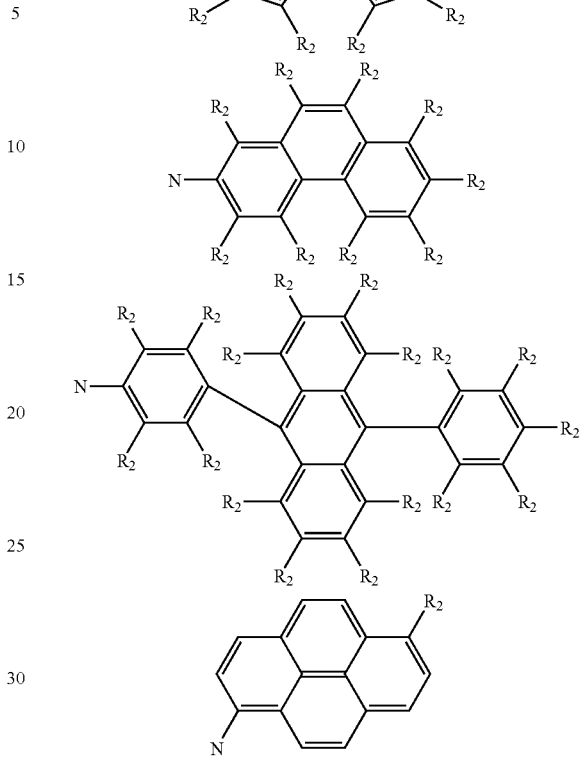

where R and $R_2$ may be formed with one selected from a group consisting of H, an alkyl group of C1 to C8, an alkoxy group, an aryl group, an alkenyl group, an arylene group, an alkylene group, and $SiR_13$ ($R_1$ is an alkyl group of C1 to C8) or combinations thereof, and the R and $R_2$ may be different from each other.

A dye-sensitized solar cell may comprise the above-described dyes.

Hereinafter, implementations of this document will be described with reference to the accompanying drawings.

FIG. 1 is a cross-sectional view illustrating a dye-sensitized solar cell in an implementation of this document.

Referring to FIG. 1, a dye-sensitized solar cell 100 has a sandwich structure in which surfaces of a first electrode 120 and a second electrode 140 are coupled to each other, specifically, has a structure in which the first electrode 120 is positioned on a first substrate 110 and in which the second electrode 140 faces on a second substrate 150 opposite to the first electrode 120.

An optical absorption layer 130 comprising an electrolyte 131, semiconductor particles 132, and dyes 133 adsorbed to the semiconductor particles 132 are positioned between the first electrode 120 and the second electrode 140.

The first substrate 110 is made of glass or plastic and as material of the first substrate 110, a material having a transmittance to apply external light is not particularly limited. Here, plastic may comprise, for example, polyethylene terephthalate (PET), polyethylene naphthalate (PEN), polycarbonate (PC), polypropylene (PP), polyimide (PI), traacetyl cellulose (TAC), or a copolymer thereof.

Here, the first substrate 110 may be doped with a material selected from a group consisting of titanium, indium, gallium, and aluminum.

The first electrode 120 may comprise a conductive metal oxide film.

Here, the conductive metal oxide film can be selected from a group consisting of indium tin oxide (ITO), fluorine tin oxide (FTO), ZnO—(Ga2O3 or Al2O3), tin-based oxide, antimony tin oxide (ATO), zinc oxide (ZnO), and a mixture thereof, and more preferably, the conductive metal oxide film can use F:SnO2.

The optical absorption layer 130 comprises an electrolyte 131, semiconductor particles 132, and dyes 133.

The electrolyte 131 can use a redox electrolyte, specifically, a halogen oxidation-reduction electrolyte composed of a halogen compound having halogen ions as counterions and halogen molecules; a metal oxidation-reduction electrolyte of a metal complex or the like such as ferrocyanate-ferrocyanate, ferrocene-ferricinium ions, or a cobalt complex; and an organic oxidation-reduction electrolyte such as alkylthiol-alkyldisulfide, viologen dyes, or hydroquinone-quinone. Preferably, the electrolyte 131 can use a halogen oxidation-reduction electrolyte.

As the halogen molecules in a halogen oxidation-reduction electrolyte composed of halogen compound-halogen molecules, iodine molecules are preferable. Further, as the halogen compound having halogen ions as counterions, halogenated metal salts such as LiI, NaI, CaI2, MgI2, and CuI, organic ammonium salts of halogens such as tetraalkylammonium iodide, imidazolium iodide, and pyridinium iodide, or I2 may be used.

Further, when the redox electrolyte is formed in a solution form comprising the redox electrolyte, the redox electrolyte uses a cell-chemically inert solvent as a solvent thereof. The redox electrolyte may comprise, for example, acetonitrile, propylene carbonate, ethylene carbonate, 3-methoxypropionitrile, methoxyacetonitrile, ethylene glycol, propylene glycol, diethylene glycol, triethylene glycol, butylrolactone, dimethoxyethane, dimethyl carbonate, 1,3-dioxolane, methyl formate, 2-methyl tetrahydrofuran, 3-methoxy-oxazoliridine-2-one, sulphorane, tetrahydrofuran, and water. Preferably, the redox electrolyte may comprise acetonitrile, propylene carbonate, ethylene carbonate, 3-methoxypropionitrile, ethylene glycol, 3-methoxy-oxazoliridine-2-one, and butylrolactone. These solvents can be used as one or a combination thereof.

The semiconductor particle 132 can use a compound semiconductor or a compound having a perovskite structure in addition to an element semiconductor represented as silicon.

The semiconductor may be an n-type semiconductor for providing an anode current as a conduction band electron is used as a carrier in a light excited state. The compound semiconductor can use a metal oxide selected from a group consisting of titan, tin, zinc, tungsten, zirconium, gallium, indium, yttrium, niobium, tantalum, and vanadium, preferably, a titan oxide, a tin oxide, a zinc oxide, a niobium oxide, titan oxide strontium, or mixtures thereof, more preferably, an anatase-type titanium oxide. The kinds of the semiconductors are not limited thereto, and the semiconductor may use one or a combination thereof.

Further, an average particle diameter of the semiconductor particles 132 is 1 to 500 nm, preferably 1 to 100 nm. Further, the semiconductor particles 132 may be used by mixing or stacking semiconductor particles having a large particle diameter and a small particle diameter.

The semiconductor particles 132 can be manufactured by coating, drying, curing, or plastic working, on a substrate, a paste containing particles that can be obtained by forming semiconductor particles in a thin film on a substrate through directly spraying, electrically extracting a thin film of semiconductor particles using a substrate as a electrode, or hydrolyzing a slurry of semiconductor particles or precursors of semiconductor particles.

Dyes 133 for generating excited electrons by absorbing external light can be adsorbed on a surface of the semiconductor particles 132.

The optical absorption layer 130 can have a thickness of 15 μm or less, preferably 1 to 15 μm.

The second electrode 140 can be positioned on the optical absorption layer 130. The second electrode 140 comprises a transparent electrode 141 and a catalyst electrode 142.

The transparent electrode 141 is made of a transparent material such as an indium tin oxide, fluoro tin oxide, antimony tin oxide, zinc oxide, tin oxide, and ZnO—(Ga2O3 or Al2O3).

The catalyst electrode 142 performs a function of activating a redox couple and can use a conductive material such as platinum, gold, ruthenium, palladium, rhodium, iridium, osmium, carbon, titan oxide, and a conductive polymer.

Further, for the purpose of improving a catalyst effect of oxidation and reduction, it is preferable that the catalyst electrode 142 facing the first electrode 120 increases a surface area with a minute structure. For example, it is preferable that the catalyst electrode 142 formed with lead or gold is in a black state, and the catalyst electrode 142 formed with carbon is in a porous state. Particularly, a platinum black state can be formed by an anode oxidation method of platinum and a chloroplatinic acid processing, and carbon of a porous state can be formed by sintering of carbon particles, or by firing of an organic polymer.

Like the first substrate 110, the second substrate 150 is made of glass or plastic. The plastic may comprise, for example polyethylene terephthalate, polyethylene naphthalate, polycarbonate, polypropylene, polyimide, and triacetyl cellulose.

When sun light is applied to the dye-sensitized solar cell 100 having such a structure, photons are first absorbed to the dyes 133 within the optical absorption layer 130, and thus the dyes 133 form electron-hole pairs by performing a electrode transition from a ground state to an excited state, electrons of an excited state are injected into a conduction band of an interface of the semiconductor particles 132, and the injected electrons are transferred to the first electrode 120 through the interface and then are moved to the second electrode 140, which is an opposite electrode through an external circuit.

The dyes 133 oxidized by an electron transition are reduced by ions of a redox couple within the electrolyte 131 and the oxidized ions perform a reduction reaction with electrons, having reached an interface of the second electrode 140 for charge neutrality and thus the dye-sensitized solar cell 100 operates.

Hereinafter, the dyes 133 used in the dye-sensitized solar cell 100 in an implementation of this document will be described in detail.

The dyes for the dye-sensitized solar cell in an implementation of this document have a structure of chemical formula 1.

[Chemical formula 1]

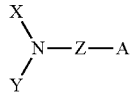

In chemical formula 1, X and Y each are substituents comprising an independently substituted or unsubstituted aromatic hydrocarbon group, a substituted or unsubstituted aromatic heterocyclic group, and combinations thereof, and at least one of the X and Y is a pyrene derivative substituted with an alkyl group or an aryl group and comprises a substituted aromatic group, Z is a substituted or unsubstituted aromatic hydrocarbon group, a substituted or unsubstituted heterocyclic group, a vinyl group, and a substituted or unsubstituted polyvinyl group, and A is an acid functional group.

The X and Y each may be a substituent comprising an independently substituted or unsubstituted aromatic hydrocarbon group having a carbon number of 5 to 20, a substituted or unsubstituted aromatic heterocyclic group, and combinations thereof, and at least one of the X and Y may comprise a pyrene derivative substituted with one selected from a group consisting of an alkyl group, an alkoxy group, an aryl group, an alkenyl group, an arylene group, and an alkylene group.

The X and Y may comprise a substituent selected from a group consisting of alkyl, alkoxy, an aryl group, an arylene group, an alkenyl group, and combinations thereof.

The Z may comprise a substituent selected from a group consisting of thiophene, a vinyl group, a polyvinyl group, benzene, naphthalene, anthracene, fluorene, biphenyl, pyran, pyrrole, carbazole, and combinations thereof.

The Z may be a substituent selected from a group consisting of alkyl, alkoxy, an aryl group, an alkenyl group, an arylene group, an alkylene group, and combinations thereof.

The A may comprise a substituent selected from a group consisting of a carboxylic acid group, a phosphorous acid group, a sulfonic acid group, a phosphinic acid group, a hydroxy acid group, an oxycarboxylic acid group, and combinations thereof.

The X—N—Y may be one of the following compounds.

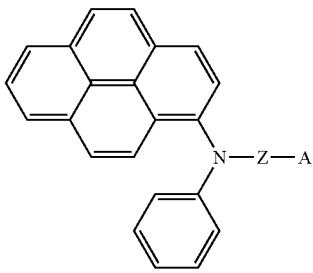

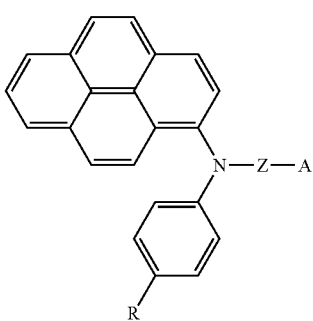

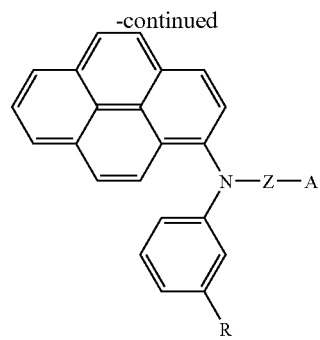

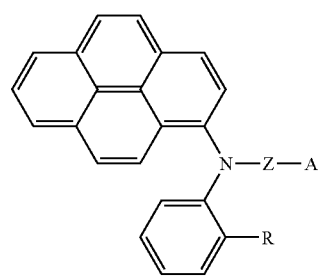

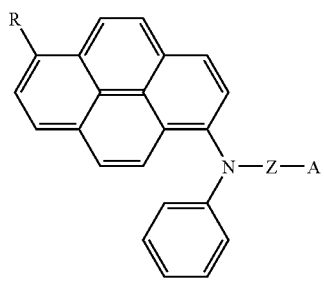

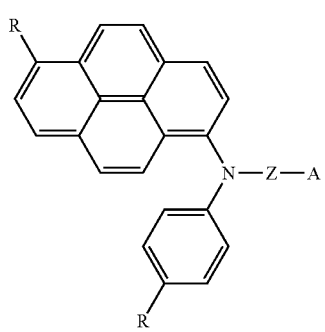

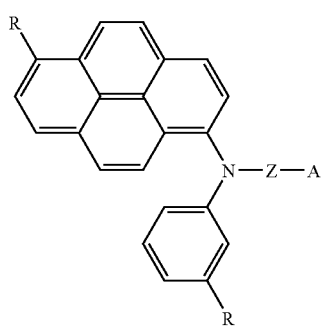

-continued
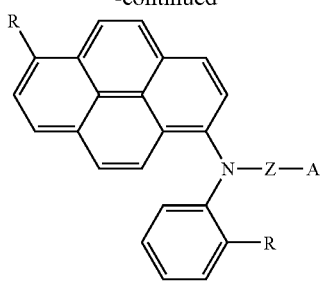
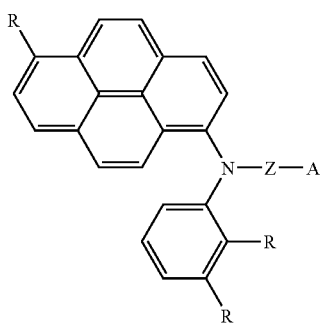
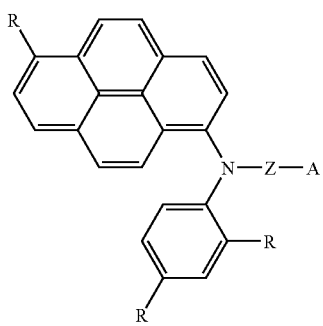
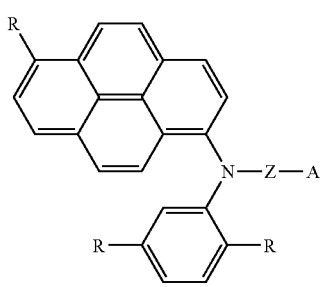
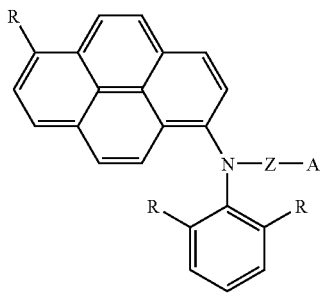
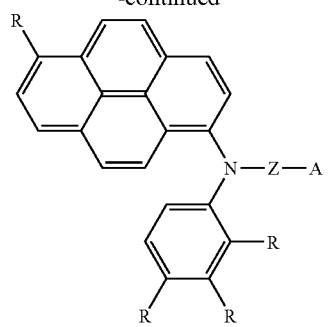
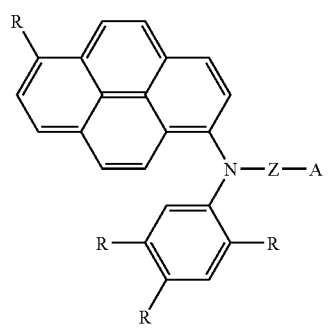
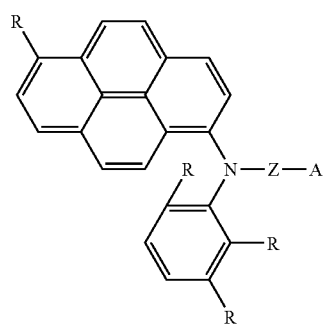
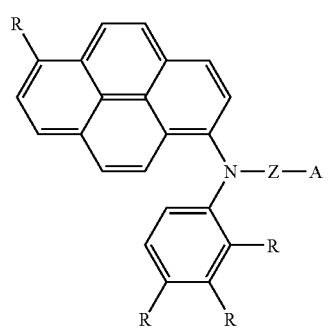
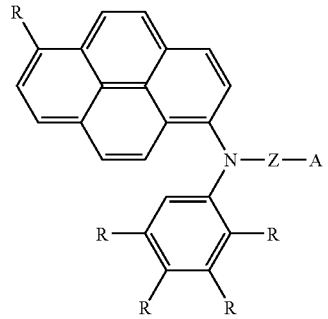

-continued

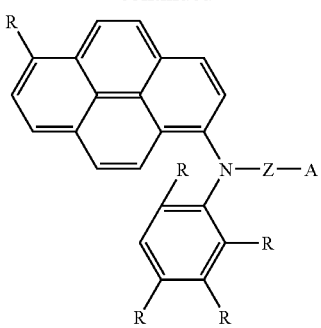

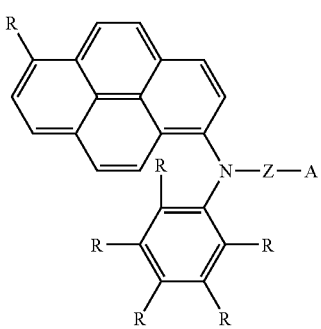

where R may be formed with one selected from a group consisting of H, an alkyl group of C1 to C8, an alkoxy group, an aryl group, an alkenyl group, an arylene group, an alkylene group, and SiR13 (R1 is an alkyl group of C1 to C8) or combinations thereof, and the R may be different from each other,

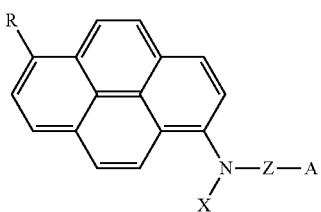

where N—X may be one of the following compounds,

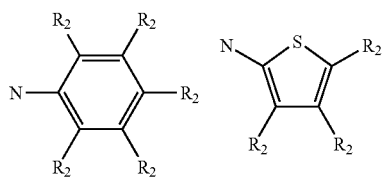 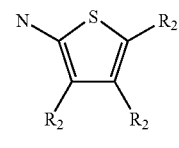

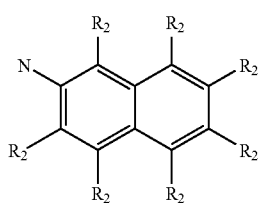

-continued

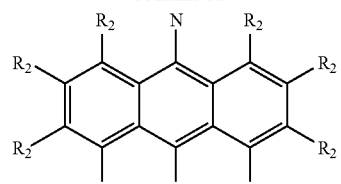

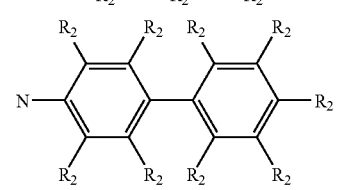

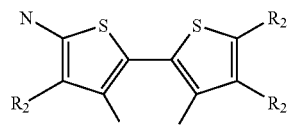

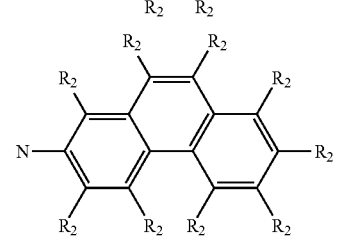

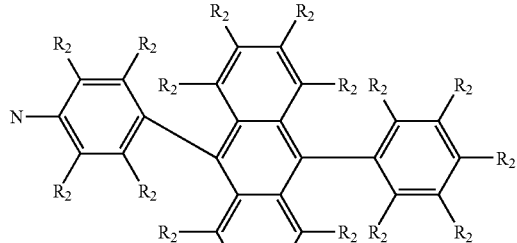

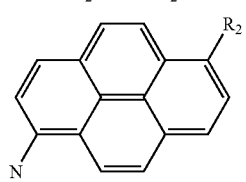

where R and R2 are formed with one selected from a group consisting of H, an alkyl group of C1 to C8, an alkoxy group, an aryl group, an alkenyl group, an arylene group, an alkylene group, and SiR13 (R1 is an alkyl group of C1 to C8) or combinations thereof, and the R and R2 may be different from each other.

A dye-sensitized solar cell in an implementation of this document may comprise the above-described dyes.

Hereinafter, for a better understanding of this document, implementations are described. However, the implementations exemplify this document and this document is not limited by the implementations.

Implementation 1: Synthesis of Dye

Dyes for a dye-sensitized solar cell of this document were synthesized through the following reaction.

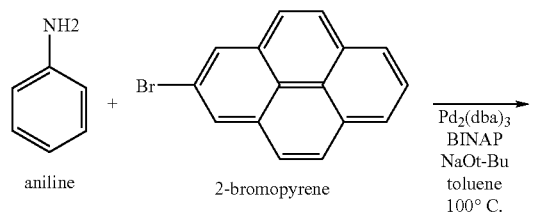

aniline + 2-bromopyrene → (Pd₂(dba)₃, BINAP, NaOt-Bu, toluene, 100° C.)

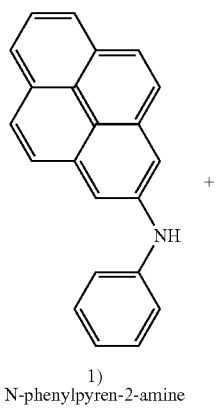

1) N-phenylpyren-2-amine

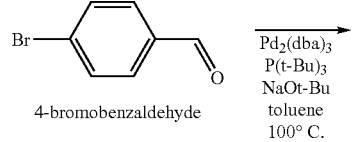

4-bromobenzaldehyde → (Pd₂(dba)₃, P(t-Bu)₃, NaOt-Bu, toluene, 100° C.)

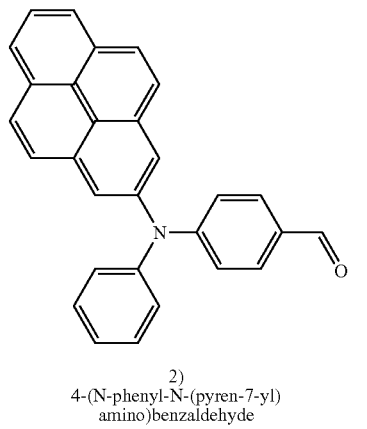

2) 4-(N-phenyl-N-(pyren-7-yl)amino)benzaldehyde

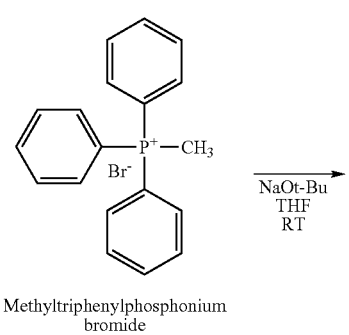

Methyltriphenylphosphonium bromide → (NaOt-Bu, THF, RT)

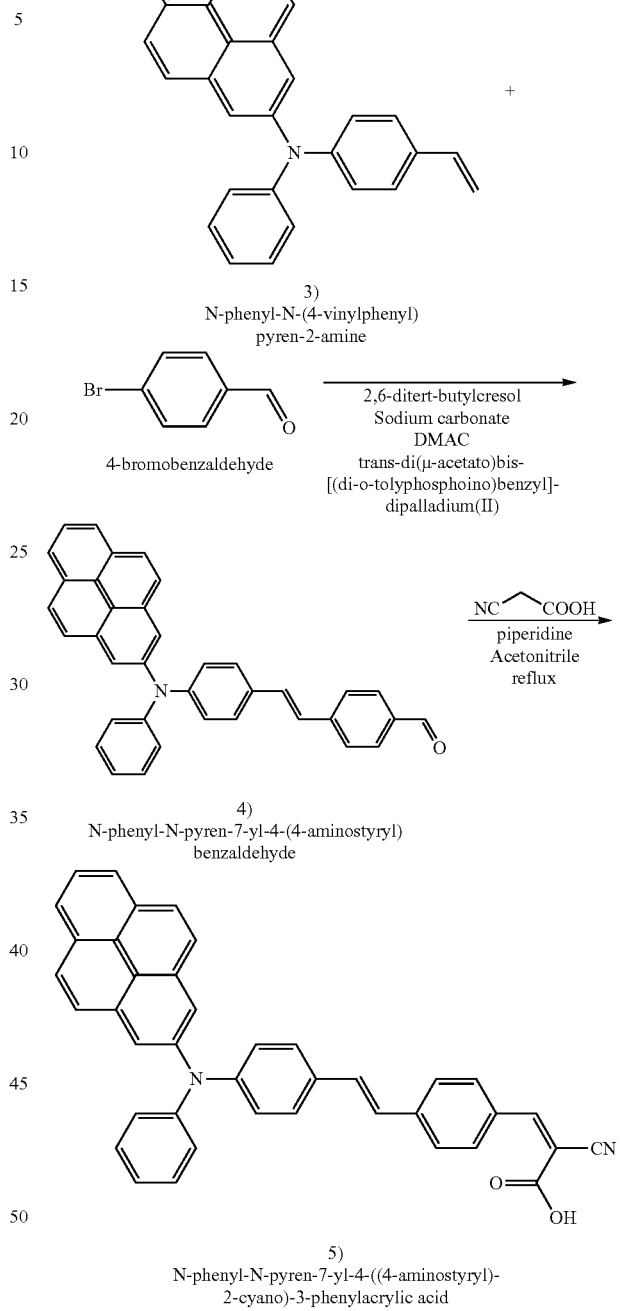

3) N-phenyl-N-(4-vinylphenyl)pyren-2-amine 4-bromobenzaldehyde → (2,6-ditert-butylcresol, Sodium carbonate, DMAC, trans-di(μ-acetato)bis-[(di-o-tolyphosphoino)benzyl]-dipalladium(II))

4) N-phenyl-N-pyren-7-yl-4-(4-aminostyryl)benzaldehyde → (NC-CH₂-COOH, piperidine, Acetonitrile, reflux)

5) N-phenyl-N-pyren-7-yl-4-((4-aminostyryl)-2-cyano)-3-phenylacrylic acid

1) Production of N-phenylpyrene-2-amine

In a three-neck-round floor flask of 250 ml, after 127.5 m mole of aniline, 102 m mole of 2-bromopyrene, 1.53 m mole of tris(dibenzyllidene acetone)dipalladium, 3.06 m mol of BINAP (2,2'-bis(disphenylphosphino)-1,1'-binaphthyl, and 132.6 m mole of sodium-tert-butoxide were melted in 100 mL of toluene and they were mixed for 24 hours in a bath of 1000, when a reaction was terminated, toluene was removed from a reaction mixture and then the reaction mixture was extracted using dichloromethane and water and distilled under a reduced pressure, a solvent of a solution passing through a silica gel column was distilled under a reduced pressure, and thus 5.5 g of an N-phenylpyrene-2-amine liquid was obtained.

2) Production of 4-(N-phenyl-N-(pyrene-7-one) amino)benzaldehyde

In a three-neck-round floor flask of 250 ml, after 22.8 m mol of N-phenylpyrene-2-amine, 29.64 m mole of 4-bromobenzaldehyde, 0.342 m mole of tris(dibenzyllidene acetone)dipalladium, 0.684 m mole of tris-tert-butyl phosphine, and 29.64 m mole of sodium-tert-butoxide were melted in 100 mL of toluene and they were mixed for 24 hours in a bath of 100°, when a reaction was terminated, toluene was removed from a reaction mixture, the reaction mixture was extracted using dichloromethane and water and distilled under a reduced pressure, a solvent of a solution passing through a silica gel column was distilled under a reduced pressure, and thus 4.1 g of a 4-(N-phenyl-N-(pyrene-7-one) amino)benzaldehyde liquid was obtained.

3) Production of N-phenyl-N-(4-vinylphenyl)pyrene-2-amine

In a three-neck-round floor flask of 250 ml in which a dropping funnel of 100 ml is mounted, after 19 m mol of sodium-tert-butoxide was melted in 100 ml of anhydrous tetrahydrofuran, 17.8 m mol of methyl triphenyl phosphonium bromide was slowly added to a solution. When a color of the solution was changed to dark yellow and a color change of the solution was no longer observed, 4-(N-phenyl-N-(pyrene-7-one)amino)benzaldehyde was melted in 30 ml of anhydrous tetrahydrofuran and slowly added thereto. After a reaction mixture was mixed for about 12 hours in a room temperature, the anhydrous tetrahydrofuran is removed from the reaction mixture, the reaction mixture was extracted using dichloromethane and n-hexane and distilled under a reduced pressure, then a solvent of a solution passing through a silica gel column was distilled under a reduced pressure, and thus 3.0 g of N-phenyl-N-(4-vinylphenyl)pyrene-2-amine was obtained.

4) Production of N-phenyl-N-pyrene-7-one-4-(4-aminostyryl)benzaldehyde

In a two-neck-round floor flask of 100 ml, 8.7 m mole of N-phenyl-N-(4-vinylphenyl)pyrene-2-amine, 17.4 m mole of 4-bromobenzaldehyde, 0.87 m mole of 2,6-di-tert-butyl-cresol, 9.57 m mole of sodium-tert-butoxide, 0.087 m mole of trans-di(μ-acetato)bis[(di-o-tolylphosphoino)benzyl]-dipalladium (II) were melted in 50 mL of N,N-dimethylacetamide and then they were mixed for 24 hours in a bath of 80°. When a reaction was terminated, glass filtering is performed using silica gel and sellaite, then N,N-dimethylacetamide was removed from the reaction mixture by distilling under a reduced pressure. Thereafter, the reaction mixture was extracted using dichloromethane and n-hexane and distilled under a reduced pressure, then a solvent of a solution passing through a silica gel column was distilled under a reduced pressure, and thus 2.5 g of N-phenyl-N-pyrene-7-one-4-(4-aminostyryl)benzaldehyde was obtained.

5) Production of N-phenyl-N-pyrene-7-one-4-((4-aminostyryl)-2-cyano)-3-phenyl acrylic acid In a two-neck-round floor flask of 100 ml, 4.2 m mol of N-phenyl-N-pyrene-7-one-4-(4-aminostyryl)benzaldehyde, 6.3 m mole of 2-cyanoacetic acid, and 10.5 m mole of piperidine were melted in 50 mL of acetonitrile and reflowed for 12 hours. When a reaction is terminated, acetonitrile is removed from a reaction mixture, the reaction mixture was extracted using dichloromethane and methanol and distilled under a reduced pressure, then a solvent of a solution passing through a silica gel column was distilled under a reduced pressure, then the reaction mixture was precipitated and filtered in methanol, and thus 2.0 g of N-phenyl-N-pyrene-7-one-4-((4-aminostyryl)-2-cyano)-3-phenyl acrylic acid was obtained.

Implementation 2: Production of Dye-Sensitized Solar Cell

1) Production of Working Electrode

Florine-doped tin oxide coated conduction glass (FTO glass, Pilkington, TEC7) is cut in a size of 2 cm×1.5 cm and after supersonic wave decomposition washing for the FTO glass is performed with a glass cleaning agent for 10 minutes, soapy water was completely removed from the FTO glass using distilled water. Thereafter, supersonic wave decomposition washing for the FTO glass was repeated 2 times for 15 minutes with ethanol. Thereafter, after completely rinsing with anhydrous ethanol, the FTO glass was dried in an oven of 100°. In order to improve a contact force with TiO2, the FTO glass was soaked for 40 minutes in 40 mM of a titanium (□) chloride solution in a temperature of 70° and washed with distilled water, and water on the FTO glass was completely dried in the oven of 100°. Thereafter, a titania (TiO2) paste (18-NR) of CCIC company was coated on the FTO glass using a mask (200 mesh) having a size of 9 mm×9 mm with a screen printer. After the coated film was dried for 20 minutes in the oven of 100°, the process was repeated 3 times. Thereafter, by firing the coated film for 60 minutes in a temperature of 450°, a TiO2 film having a thickness of about 10 μm was obtained. By soaking the TiO2 film in which a heat treatment process was terminated for 24 hours in an anhydrous ethanol solution of synthesized dyes having a density of 0.5 mM, dyes can be adsorbed. (At this time, when dyes were not melted in anhydrous ethanol, solvent that can melt the dyes can be used.) After adsorption is terminated, dyes that were not adsorbed were completely washed with anhydrous ethanol and dried using a heat gun.

2) Production of Counter Electrode

In a FTO glass having a size of 2 cm×1.5 cm, two holes for injecting an electrolyte were bored using a diamond drill (Dremel multipro395) of Φ0.7 mm. Thereafter, the holes were washed and dried with the same method as a washing method suggested in a working electrode. Thereafter, a hydrogen hexachloroplatinate (H2PtCl6)2-propanol solution was coated on the FTO glass and the FTO glass was fired for 60 minutes in a temperature of 450°.

3) Production of Sandwich Cell

After a surlyn (SX1170-25 hot melt) cut in a quadrangular belt shape is put between the working electrode and the counter electrode and two electrodes are attached using a clip and an oven of 100°, and then an electrolyte is injected through two small holes in the counter electrode, by sealing with a surlyn strip and a cover glass, a sandwich cell was produced. In this case, an electrolyte solution was produced with 0.1M of LiI, 0.05M of 12, 0.6M of 1-hexyl-2,3-dimethylimideazolium iodide and 0.5M of 4-tert-butylpyridine using 3-methoxypropionitrile as a solvent.

4) Measurement of Photocurrent-Voltage

In the produced sandwich cell, a current-voltage curved line was obtained by radiating light with an Xe lamp (Oriel, 300 W Xe arc lamp) in which an AM 1.5 solar simulating filter is mounted and using an M236 source measure unit (SMU, Keithley). A potential had a range of from −0.8V to 0.2V, and light had intensity of 1000 W/m².

Hereinafter, experimental examples of the solar cell produced in the implementations are described.

Experimental Example 1

A solar cell was manufactured using dyes represented with Experimental Example 2.

[Chemical formula 2]

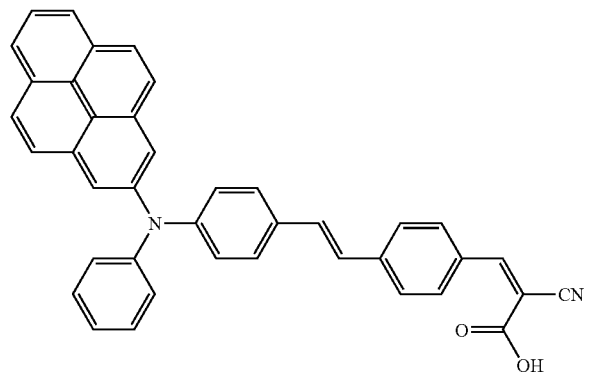

Experimental Example 2

A solar cell was manufactured using dyes represented with Experimental Example 3.

[Chemical Formula 3]

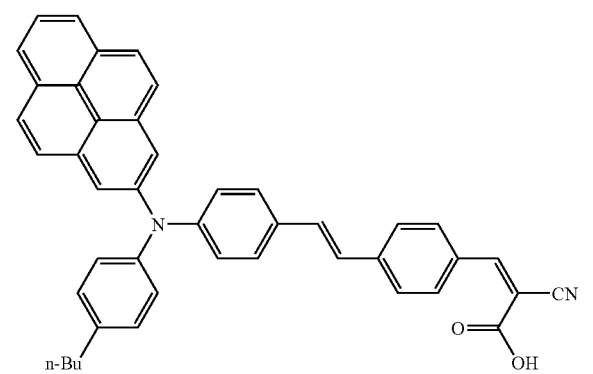

Experiment Example 3

A solar cell was manufactured using dyes represented with Experimental Example 4.

[Chemical Formula 4]

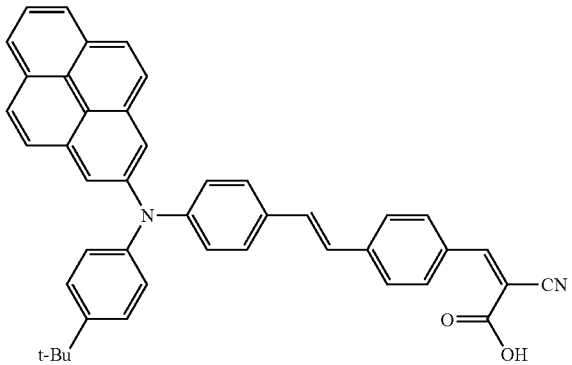

Comparative Example

A solar cell was manufactured using dyes represented with Experimental Example 5.

[Chemical formula 5]

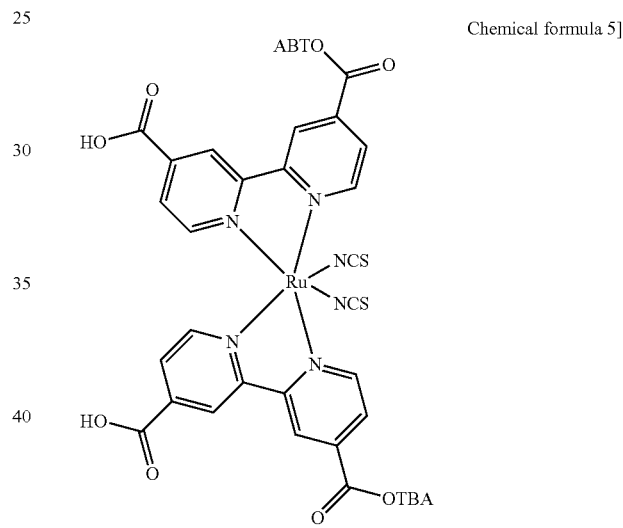

Measured results of a short-circuit photocurrent density (Jsc), an open circuit voltage (Voc), a fill factor (FF), and photoelectric conversion efficiency (PCE) of the dye-sensitized solar cell manufactured according to Experimental Examples 1 to 3 and Comparative Example were represented in Table 1. In the Experimental Examples and Comparative Example, measurement was performed two times under the same condition.

TABLE 1

| | # | Area (cm²) | Jsc (mA) | Voc (V) | FF (%) | PCE (%) |
|---|---|---|---|---|---|---|
| Experimental Example 1 | 1 | 0.81 | 9.00 | 0.625 | 54.05 | 3.04 |
| | 2 | 0.81 | 9.18 | 0.657 | 55.99 | 3.38 |
| Experimental Example 2 | 1 | 0.81 | 9.20 | 0.648 | 53.01 | 3.16 |
| | 2 | 0.81 | 9.68 | 0.655 | 52.15 | 3.30 |
| Experimental Example 3 | 1 | 0.81 | 9.29 | 0.643 | 53.24 | 3.18 |
| | 2 | 0.81 | 9.43 | 0.650 | 54.02 | 3.31 |
| Comparative example | 1 | 0.81 | 13.88 | 0.634 | 40.85 | 3.60 |
| | 2 | 0.81 | 13.09 | 0.664 | 41.60 | 3.62 |

As shown in Table 1, the solar cell manufactured according to Experimental Examples 1 to 3 of this document represents an open voltage Voc similar to Comparative example and has photoelectric conversion efficiency (PCE) corresponding to 80% of that of Comparative example using dyes N719 having highest efficiency up to now.

Therefore, dyes for a dye-sensitized solar cell and a solar cell comprising the dyes in an implementation of this document have photoelectric conversion efficiency similar to a conventional organic metal solar cell while having a much cheaper production cost than the conventional organic metal solar cell having an expensive production cost and have a more extended lifetime than that of the organic metal dyes.

The foregoing embodiments and advantages are merely exemplary and are not to be construed as limiting this document. The present teaching can be readily applied to other types of apparatuses. The description of the foregoing embodiments is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures. Moreover, unless the term "means" is explicitly recited in a limitation of the claims, such limitation is not intended to be interpreted under 35 USC 112 (6).

What is claimed is:

1. Dyes for a dye-sensitized solar cell having a structure of chemical formula 1:

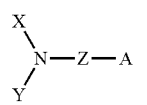

[chemical formula 1]

wherein each of X and Y independently comprises a substituent, comprising a substituted or unsubstituted aromatic hydrocarbon group, a substituted or unsubstituted aromatic heterocyclic group, and combinations thereof, and at least one of the X and Y comprises a pyrene derivative substituted with an alkyl group or an aryl group, and Z comprises a stilbene and A comprises an acid functional group.

2. The dyes of claim 1, further comprising, wherein each of the X and Y independently comprises a substituent, comprising a substituted or unsubstituted aromatic hydrocarbon group having a carbon number of 5 to 20, a substituted or unsubstituted aromatic heterocyclic group, and combinations thereof, and at least one of the X and Y comprises a pyrene derivative substituted with one selected from a group consisting of an alkoxy group, an alkenyl group, an arylene group, and an alkylene group.

3. The dyes of claim 1, wherein the X and Y each comprise a substituent selected from a group consisting of alkyl, alkoxy, an aryl group, an arylene group, an alkylene group, and combinations thereof.

4. The dyes of claim 1, wherein the A comprises a substituent selected from a group consisting of a carboxylic acid group, a phosphorous acid group, a sulfonic acid group, a phosphinic acid group, a hydroxy acid group, an oxycarboxylic acid group, and combinations thereof.

5. The dyes of claim 1, wherein the X—N—Y is one of the following compounds:

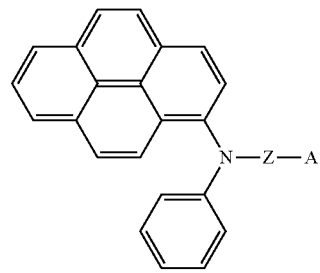

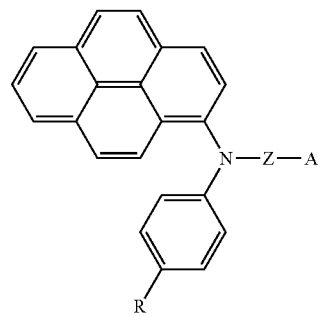

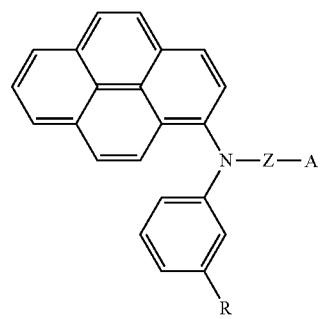

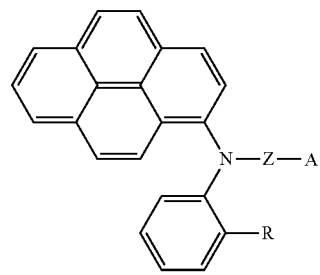

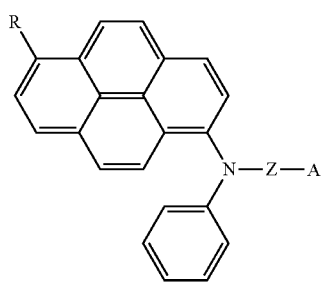

25
-continued
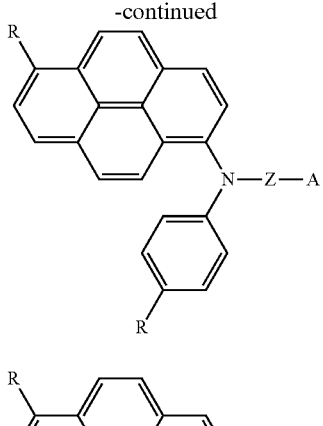
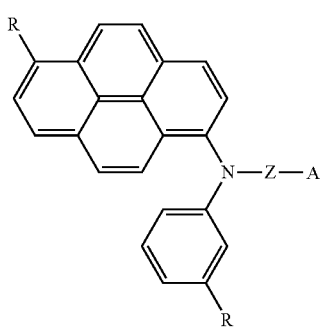
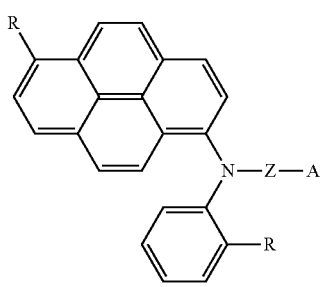
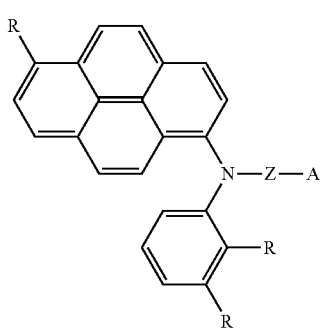
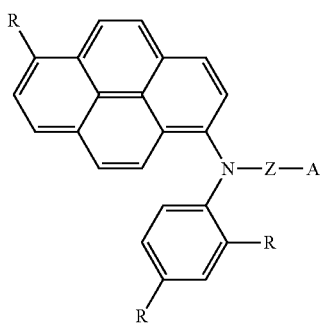
26
-continued
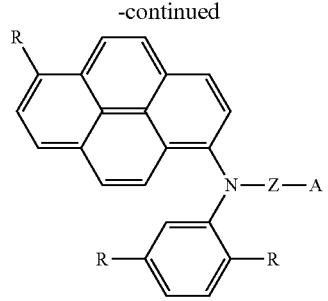
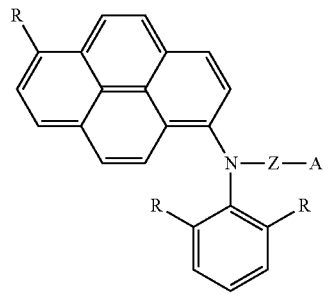
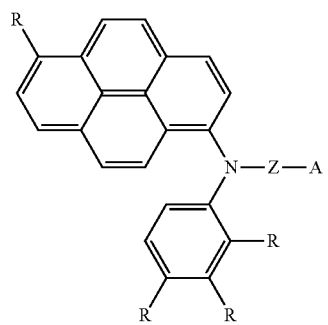
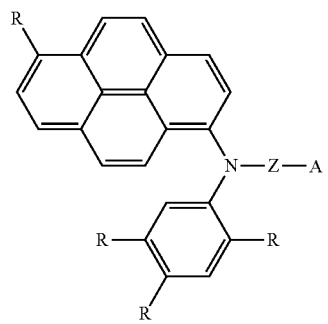
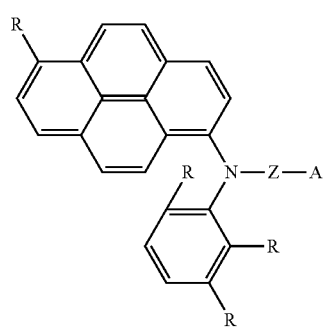

27
-continued
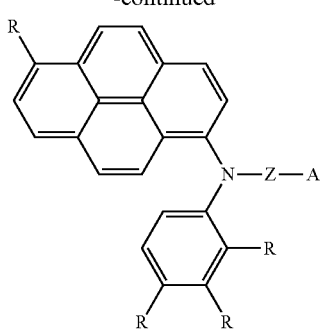
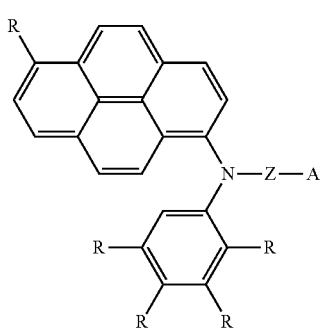
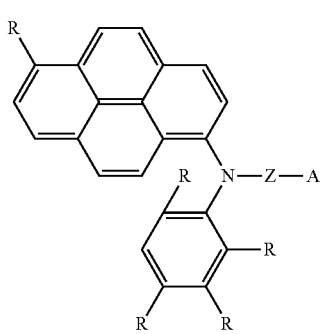
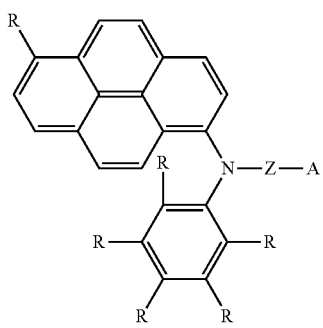
where R is formed with one selected from a group consisting of H, an alkyl group of C1 to C8, an alkoxy group, an aryl group, an alkenyl group, an arylene group, an alkylene group, and $SiR_13$ ($R_1$ is an alkyl group of C1 to C8) or combinations thereof, and the R is different from each other,
28
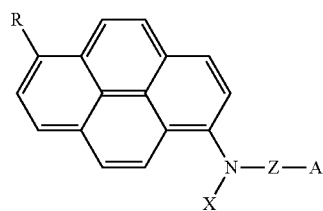
where N—X is one of the following compounds,
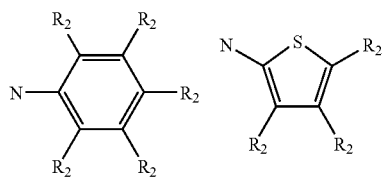
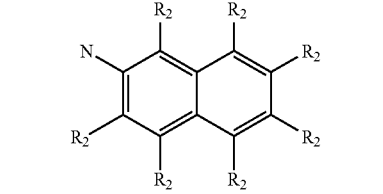
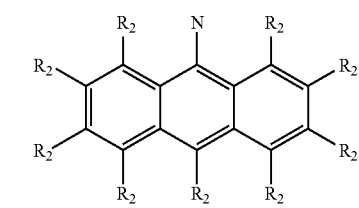
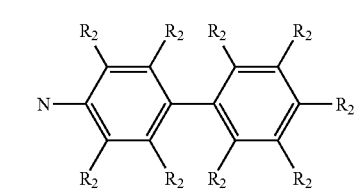
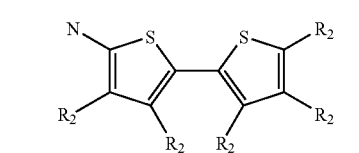
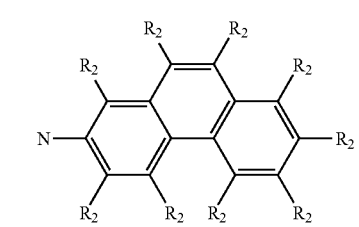

-continued
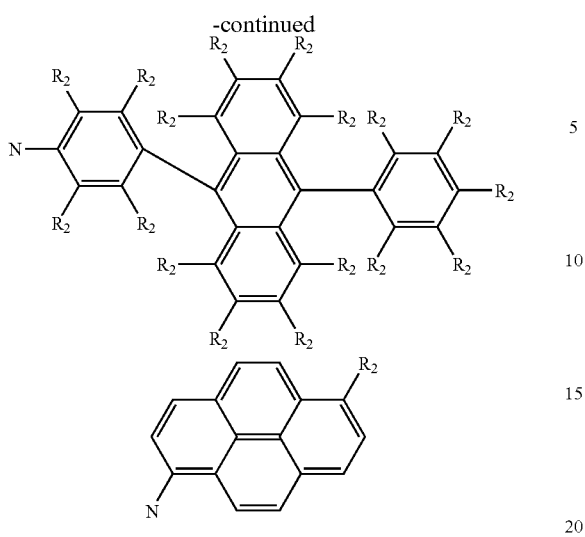
where R and $R_2$ are formed with one selected from a group consisting of H, an alkyl group of C1 to C8, an alkoxy group, an aryl group, an alkenyl group, an arylene group, an alkylene group, and $SiR_13$ ($R_1$ is an alkyl group of C1 to C8) or combinations thereof, and the R and $R_2$ are different from each other.
* * * * *